US00PP16599P2

(12) United States Plant Patent
Zaiger et al.

(10) Patent No.: US PP16,599 P2
(45) Date of Patent: May 30, 2006

(54) INTERSPECIFIC TREE NAMED 'AUTUMN SPRITE'

(50) Latin Name: *Prunus armeniaca×Prunus salicina*
Varietal Denomination: Autumn Sprite

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 102 days.

(21) Appl. No.: 11/027,211

(22) Filed: Jan. 3, 2005

(51) Int. Cl.
*A01H 5/00* (2006.01)

(52) U.S. Cl. ..... Plt./180
(58) Field of Classification Search ..... Plt./180
See application file for complete search history.

*Primary Examiner*—Anne Marie Grunberg
*Assistant Examiner*—June Hwu

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Regular and productive bearer of medium to large fruit.
2. Vigorous, semi-spreading tree growth.
3. Fruit with excellent flavor and eating quality.
4. Fruit with an attractive yellow-orange skin color.
5. Having firmer flesh than most commercial apricot varieties.
6. Fruit holding firm on the tree 10–12 days after maturity (shipping ripe).

1 Drawing Sheet

BACKGROUND OF THE VARIETY

Field of The Invention

In the field of plant genetics, we conduct an extensive and continuing plant-breeding program, including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific, plum and apricot trees, which are known to us, and mentioned herein, are 'Flavor King' Interspecific (U.S. Plant Pat. No. 8,026), 'Mariposa' Plum (U.S. Plant Pat. No. 111), 'Red Beaut' Plum (U.S. Plant Pat. No. 2,539), 'Patterson' Apricot (U.S. Plant Pat. No. 2,877), 'Modesto' Apricot (U.S. Plant Pat. No. 2,543), 'Tracy' Apricot (U.S. Plant Pat. No. 3,062) and 'Autumn Glory' Apricot (non-patented).

ORIGIN OF THE VARIETY

The new and distinct variety of interspecific tree, a combination of crosses between (*Prunus armeniaca* and *Prunus salicina*), was originated by us in our experimental orchard located near Modesto, Calif. as a first generation cross between proprietary lines of immediate parents with field identification numbers '192LD95' and '63EG50'. The maternal parent (192LD95) originated from crosses of the following apricot parents, 'Patterson' (U.S. Plant Pat. No. 2,877), 'Modesto' (U.S. Plant Pat. No. 2,543), 'Autumn Glory' (non-patented), 'Tracy' (U.S. Plant Pat. No. 3,062) and the proprietary plumcot '4G436'. The paternal parent (63EG50) originated from a cross between the proprietary interspecific parent '7HC250' and the interspecific tree 'Flavor King' (U.S. Plant Pat. No. 8,026). The proprietary parent '7HC250' originated as a selected seedling from crosses of the following parents, 'Mariposa' Plum (U.S. Plant Pat. No. 111), 'Red Beaut' Plum (U.S. Plant Pat. No. 2,539) and two proprietary plumcots with field identification numbers '4G1180' and '42GA580'. A large number of these first generation crosses were budded on older trees of 'Nemaguard' Rootstock (non-patented), to induce earlier fruit production, one budded seedling exhibited desirable fruit and tree growth characteristics and was selected in 1997 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree is of large size, vigorous, semi-spreading growth and a regular bearer of medium to large size fruit with excellent flavor and eating quality. The fruit is further characterized by having an attractive yellow-orange skin color with a slight reddish pin blush, firm flesh, holding firm on the tree 10–12 days after maturity (shipping ripe) and being relatively uniform in maturity and size throughout the tree. The fruit having good handling, storage and shipping quality, with an average Brix of 15.6°. In comparison to one of its apricot parents 'Patterson' (U.S. Plant Pat. No. 2,877), the fruit of the new variety is larger in size, higher in soluble solids (Brix), is approximately 37 days later in maturity, and the tree has approximately 150 hours less winter chilling requirement. In comparison to the interspecific maternal parent (192LD95), the fruit of the new variety has firmer flesh, is slightly larger in size and is approximately 2 weeks earlier in maturity. In comparison to the fruit of the interspecific paternal parent (63 EG60), the fruit of the new variety is moderately covered with pubescence, compared to slick, smooth skin, is yellow-orange in color, compared to red and is approximately 7 weeks earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color.

Tree:

*Size.*—Large. Usually pruned to 3 to 3.5 meters in height and width for economical harvesting of fruit.

*Vigor.*—Vigorous, growth of 1.5 to 2 meters in height the first growing season. Varies with type of soil, fertility, climatic conditions and cultural practices.

*Form.*—Semi-spreading, usually pruned to vase shape.

*Branching habit.*—Semi-spreading, crotch angle approximately 40°, increases with heavy crop load.

*Productivity.*—Productive, thinning and spacing of fruit necessary, fruit set varies slightly with climatic conditions at bloom time.

*Bearer.*—Regular, 5 consecutive years of adequate fruit set, no alternate bearing observed.

*Fertility.*—Self fertile.

*Density.*—Medium dense. Pruned to vase shape to allow sunlight and air movement to center of tree to enhance fruit color and health of fruit spurs.

*Hardiness.*—Tree grown in USDA Hardiness Zone 9. Hardy in all stone fruit growing areas of California. Winter chilling requirement approximately 550 hours at or below 45° F.

Trunk:

*Size.*—Medium stocky. Average circumference 52.1 cm at 33.0 cm above ground on 7 year old tree.

*Stocky.*—Medium.

*Texture.*—Medium shaggy, increases with age of growth.

*Color.*—Varies from 5Y 7/2 to 7.5Y 6/2.

Branches:

*Size.*—Medium. Average circumference 15.2 cm at 0.7 meters above ground. Crotch angle approximately 40°, increases with heavy crop load.

*Surface texture.*—New growth smooth. Old growth medium rough.

*Lenticels.*—Average number 39 in a 25.8 square cm surface area of branch. Size — average length 4.2 mm. Average width 1.5 mm. Color varies from 10YR 8/8 to 2.5Y 8.5/6.

*Color.*—New growth varies from 10Y 7/6 to 2.5YR 5/6, varies with exposure to sunlight. Old growth varies from 5YR 4/2 to 7.5YR 3/2, varies with age of growth.

Leaves:

*Size.*—Medium. Average length 74.1 mm. Average width 53.0 mm.

*Form.*—Ovate.

*Apex.*—Acuminate.

*Base.*—Obtuse.

*Margin.*—Doubly serrate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Size — medium. Average length 28.4 mm. Average width 1.4 mm. Color varies from 2.5GY 5/8 to 2.5Y 5/8, where exposed to direct sunlight. Very shallow, longitudinal groove. Surface — glabrous.

*Glands.*—Size — small. Form — globose. Average length 0.3 mm. Average diameter 0.3 mm. Average number 2, varies from 1 to 3. Located on base of leaf blade and upper portion of petiole. Color varies from 2.5Y 5/8 to 5GY 5/6.

*Color.*—Upper surface varies from 5GY 5/8 to 5GY 3/6. Lower surface varies from 5GY 5/6 to 5GY 4/4. Midvein color varies from 2.5GY 8/6 to 5GY 8.6.

Flower buds:

*Size.*—Small to medium. Average length 11.7 mm. Average diameter 6.4 mm.

*Hardiness.*—Hardy in all stone fruit growing areas of California.

*Form.*—Conical, becoming slightly elongated just before opening.

*Pedicel.*—Very short. Average length 1.8 mm. Average width 2.3 mm. Color varies from 2.5GY 7/8 to 5GY 6/6.

*Color.*—Varies from 5RP 9/2 to 5RP 7/10.

*Number of buds per spur.*— 2 to 6, varies with age of spur.

Flower:

*Size.*—Small to medium. Average height 14.5 mm. Average diameter 22.9 mm.

*Petals.*—Number 5, alternately arranged to sepals. Size — medium. Average length 12.2 mm. Average width 10.9 mm. Obovate, narrows at point of attachment. Margin — sinuate. Color varies from 2.5RP 9/2 to 5RP 8/6, fades with age of flower.

*Sepals.*—Number 5, alternately arranged to petals. Size — small to medium. Average length 5.4 mm. Average width 3.0 mm. Triangular, apex pointed. Margin — entire. Upper and lower surface glabrous. Color — upper surface varies from 2.5R 3/6 to 2.5R 3/8. Lower surface varies from 2.5R 2/8 to 5R 2/8.

*Stamens.*—Average number per flower 30. Average filament length 9.3 mm. Filament color — N 9.5/. Anther color varies from 5Y 8.5/8 to 5Y 8/10.

*Pollen.*—Abundant, self fertile. Color varies from 2.5Y 7/10 to 5Y 7/10.

*Pistil.*—Normally 1, varies from 1 to 2. Surface — pubescent. Average length 13.7 mm. Position of stigma average of 1.6 mm above anthers. Color varies from 10Y 8.5/6 to 2.5GY 8/6.

*Fragrance.*—Very slight.

*Blooming period.*—Date of First Bloom Feb. 20, 2003. Date of Petal Fall Feb. 28, 2003, varies slightly with climatic conditions.

*Color.*—Varies from 2.5RP 9/2 to 5RP 8/6, fading as flowers age.

*Number flowers per flower bud.*—Usually 2, varies from 1 to 3.

*Pedicel.*—Average length 2.1 mm. Average width 2.3 mm. Color varies from 2.5GY 6/6 to 5GY 6/6.

Fruit:

*Maturity when described.*—Firm ripe.

*Date of first picking.*—Aug. 4, 2003.

*Date of last picking.*—Aug. 10, 2003, varies slightly with climatic conditions.

*Size.*—Medium to large. Average diameter axially 52.9 mm. Average transversely in suture plane 54.9 mm. Average across suture plane 49.1 mm. Average weight 88.0 grams, average weight varies slightly with fertility of the soil, amount of thinning and climatic conditions.

*Form.*—Globose, slightly flattened toward suture plane.

*Suture.*—Shallow, extends from base to apex.

*Ventral surface.*—Distinct, very slightly lipped.

*Apex.*—Slightly retuse.

*Base.*—Flat to slightly retuse.

*Cavity.*—Rounded to slightly elongated in suture plane. Average depth 5.0 mm. Average diameter 8.7 mm.

Stem:

*Size.*—Small. Average length 5.4 mm. Average diameter 2.4 mm.

*Color.*—Varies from 10Y 5/8 to 2.5GY 4/6.

Flesh:

*Ripens.*—Evenly.

*Texture.*—Outer surface near skin quite firm, toward pit cavity smooth, juicy.

*Fibers.*—Few, very small, tender.

*Firmness.*—Firm, much firmer than most commercial shipping varieties of apricots.

*Aroma.*—Slight.

*Amydgalin.*—Undetected.

*Eating quality.*—Excellent.

*Flavor.*—Excellent, good balance between acid and sugar.

*Juice.*—Moderate, enhances flavor.

*Brix.*—Average 15.6°, varies slightly with amount of fruit per tree and climatic conditions.

*Color.*—Varies from 6.25YR 7/12 to 6.25YR 7/14. Pit cavity varies from 5YR 6/10 to 5YR 6/12.

Skin:

*Thickness.*—Medium.

*Surface.*—Nearly smooth, some fruit very slightly waffled.

*Down.*—Moderate pubescence, short in length.

*Tendency to crack.*—None.

*Color.*—Varies from 7.5YR 7/10 to 7.5YR 7/12, darker color where exposed to direct sunlight.

*Tenacity.*—Tenacious to flesh.

*Astringency.*—None.

Stone:

*Type.*—Freestone.

*Size.*—Large. Average length 27.8 mm. Average width 21.8 mm. Average thickness 14.7 mm.

*Form.*—Obovoid.

*Base.*—Usually straight, varies from straight to rounded.

*Apex.*—Usually rounded, varies from rounded to slight point. Average length 0.6 mm.

*Surface.*—Slightly pitted throughout, a shallow groove on each side of suture. Pits vary from round to elongated.

*Sides.*—Unequal, one side extending further from suture plane.

*Ridges.*—Very small, narrow ridge next to the groove on each side of suture.

*Tendency to split.*—None.

*Color.*—Varies from 7.5YR 5/4 to 10YR 5/4.

Kernal:

*Size.*—Large. Average length 20.3 mm. Average width 15.2 mm. Average thickness 7.1 mm.

*Viability.*—Viable, complete embryo development.

*Form.*—Ovate.

*Skin color.*—Varies from 10YR 8/4 to 2.5Y 9/4 when dry.

Use:

*Dessert.*—Market — local and long distance.

Keeping quality: Good, held firm in storage 2 weeks at 38° to 42° F. without shriveling, internal breakdown of flesh or appreciable loss of eating quality.

Shipping quality: Good, showed minimal flesh bruising or skin scarring during picking, packing and shipping trails.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct interspecific tree, substantially as illustrated and described, characterized by its large size, vigorous, semi-spreading growth and being a regular and productive bearer of medium to large fruit with excellent flavor and eating quality; the fruit is further characterized by having firm flesh, holding firm on the tree 10 to 12 days after maturity (shipping ripe), is relatively uniform in size throughout the tree and, in comparison to 'Patterson' Apricot (U.S. Plant Pat. No. 2,877), is larger in size and is approximately 37 days later in maturity.

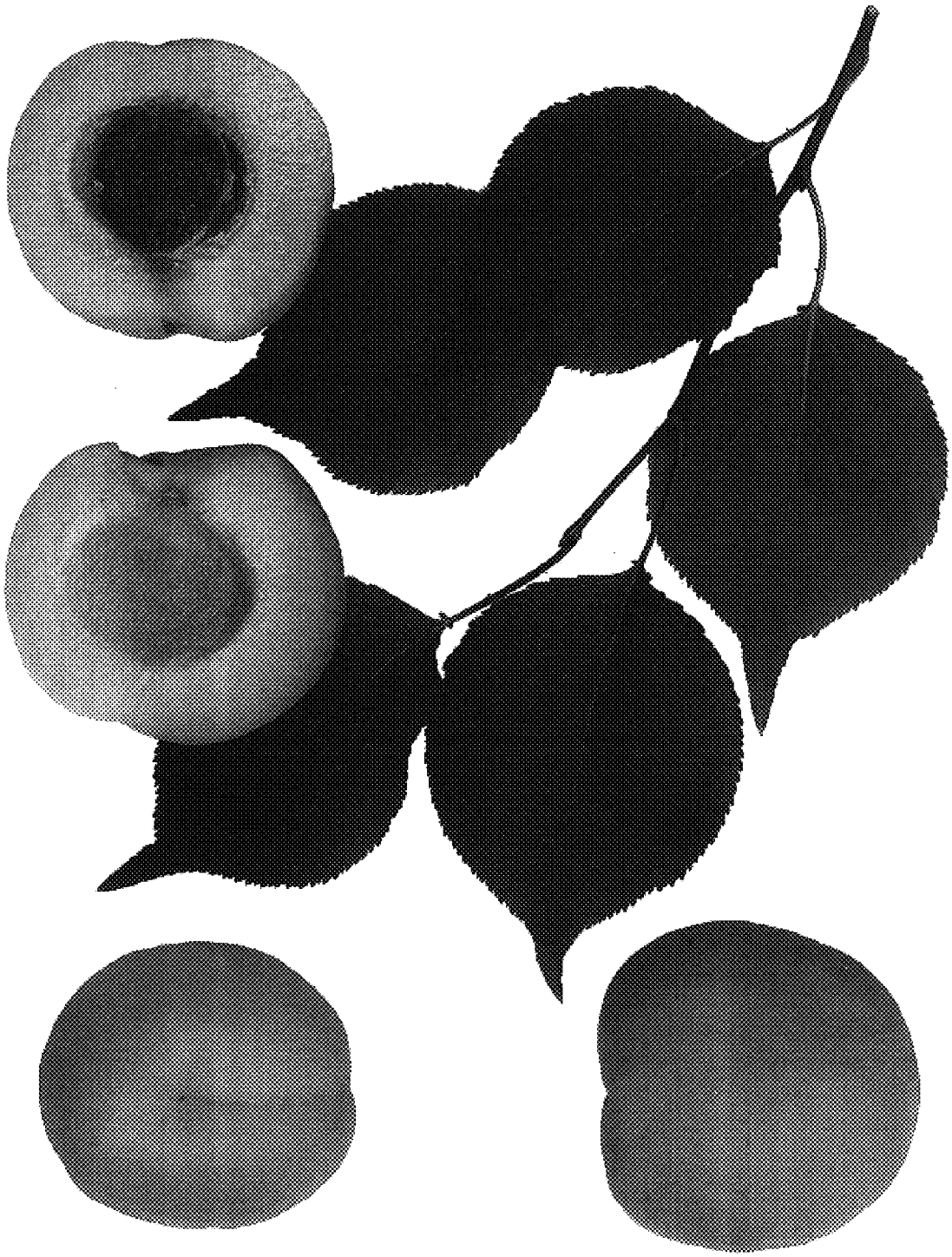

* * * * *